(12) United States Patent
Yamagoe et al.

(10) Patent No.: US 6,541,681 B1
(45) Date of Patent: Apr. 1, 2003

(54) MOUSE WITH DEFICIENCY OF GENE OF NEUTROPHIL CHEMOTACTIC FACTOR LECT2

(75) Inventors: Satoshi Yamagoe, Kashiwa (JP); Kazuo Suzuki, 663-2, Shiigi, Misaki-machi, Isumi-gun, chiba (JP); Yoichiro Iwakura, Tokyo (JP); Takeshi Saito, Tokyo (JP); Masahide Asano, Kawasaki (JP)

(73) Assignee: Kazuo Suzuki, Chiba (JP)

( * ) Notice: Subject to any disclaimer, the term of this patent is extended or adjusted under 35 U.S.C. 154(b) by 0 days.

(21) Appl. No.: 10/146,762

(22) Filed: May 16, 2002

(51) Int. Cl.$^7$ .................. A01K 67/027; A01K 67/00; G01N 33/00; C12N 15/00; C07H 21/02; C07H 21/04

(52) U.S. Cl. ............................. 800/18; 800/3; 800/8; 800/25; 800/14; 536/23.1; 536/23.5

(58) Field of Search ............... 800/18, 14; 536/23.1, 536/23.5

(56) References Cited

PUBLICATIONS

Capecchi, 1994, Scientific American, vol. 270, pp 34–41.*
Yamagoe, 1998, Gene, vol. 216, p. 171–178.*

* cited by examiner

Primary Examiner—Michael C. Wilson
Assistant Examiner—Valarie Bertoglio
(74) Attorney, Agent, or Firm—Jordan and Hamburg LLP

(57) ABSTRACT

This invention relates to a mouse with deficiency of gene of neutrophil chemotactic factor LECT2 having a function of lacking by deleting a whole or a part LECT2 gene or inserting other gene such as a selective marker gene to any portion of the LECT2 gene or replacing it with another gene(s).

4 Claims, 2 Drawing Sheets

MOUSE WITH DEFICIENCY OF GENE OF NEUTROPHIL CHEMOTACTIC FACTOR LECT2

BACKGROUND OF THE INVENTION

1. Field of the Invention

This invention is concerned with a novel animal with a deficiency of neutrophil chemotactic factor LECT2. The animal of the invention is mouse for experiment and research, which has no LECT2 protein by lacking LECT2 gene in its partial or whole gene. This invention is also concerned with the novel animal for investigation in etiology analysis and the development in therapeutic procedures for diseases of liver, bone, brain, respiratory organs, circulation organs and immune response concerning LECT2 such as hepatitis, cirrosis, hepatic cancer, regeneration of liver tissue, bone metabolism, rheumatoid arthritis, brain diseases, vasculitis, atherosclerosis, reperfusion dysfunction by eschemia, renal failure.

2. Prior Art

Liver shows an important role in the storage of substances, detoxification, host defense against infection, and homeostatis for life. When liver functions decrease in activity according to hepatic injury such as hepatitis, cirrhosis, hepatic cancer, cell proliferation hepatocytes is started for recovery to get normal function of the hepatocytes. Usually, hepatocytes do not show cell proliferation under the conditions of suppression of cell division. The cell proliferation starts on the regeneration of liver tissue by the damage of liver tissue Some cytokines such as TNF-alpha and IL-6 are related in the proliferation of hepatocytes. However, it is difficult to explain the regulation of cell proliferation of hepatocytes by only these cytokines (References 1–3). On the other hand, LECT2 expressed in hepatocytes in liver tissue may regulate liver functions (Reference 4).

LECT2 has been purified as a novel neutrophil chemotactic factor (Reference 5). It is the protein that acts in the differentiation of macrophages and is mainly expressed in liver tissue (Reference 4). mRNA and protein of LECT2 are mainly expressed in hepatocytes. This can be seen from histological observations of hepatocytes and cell lines of hepatocytes. Therefore, LECT2 seems to be related with liver functions. Indeed, the inventors show a decrease in LECT2 expression from a normal liver to a liver with cancer (References 6, 7).

ChondromodulinII has the same amino acid sequence to that of LECT2, which is the same gene and protein, showing the activation of proliferation of osteoblasts (Reference 8), suggesting that LECT2 is related with bone metabolism. Bone metabolism is essential for maintaining bone skeletons and is supported by balance between proliferation of osteoblast cells and osteocrast cells. It has not been clarified in detail, though some cytokines are related.

Thus, it has not been clarified in the etiology of diseases related with the dysfunction of the liver such as hepatitis, hepatic cancer, cirrosis, regeneration of liver tissue, autoimmune diseases, or abnormality of bone metabolism, but LECT2 may be an important agent in many important functions related with these diseases in vivo. Therefore, it is an important subject to analyze the role of LECT2 in vivo. Thus, preparation of model animal lacking LECT2 gene is strongly requested as an experimental model for investigating the effect of the subject protein lacking the LECT2 gene in its partial or whole gene.

As mentioned above, the inventors prepare the mouse lacking the LECT2 gene for analyzing the role of LECT2 in vivo. Then it will be possible to observe the physiological role of LECT2 directly. Thus, this invention of an animal model having a certain genetic background will show a clear etiology of diseases related with LECT2 and other diseases.

Procedures for dissolving the subject:

These inventors have investigated a recombination of specific vectors for LECT2 using a gene targeting method, which has been developed (9), and then this invention has been completed. Thus, this invention is concerned with mouse lacking the complete LECT2 gene by replacing the gene with a gene lacking LECT2 or another gene.

SUMMARY OF THE INVENTION

This invention is described as follows. The mouse prepared in this invention lacking the complete LECT2 gene by replacement of the gene with a gene lacking LECT2 or other genes, indicating the mouse has no LECT2 protein by lacking LECT2 gene in its partial or whole gene. The mouse in this invention is also concerned with the mouse having lack of the complete LECT2 gene in homozygotes or heterozygotes.

DESCRIPTION OF THE PREFERRED EMBODIMENT

Figure 1:
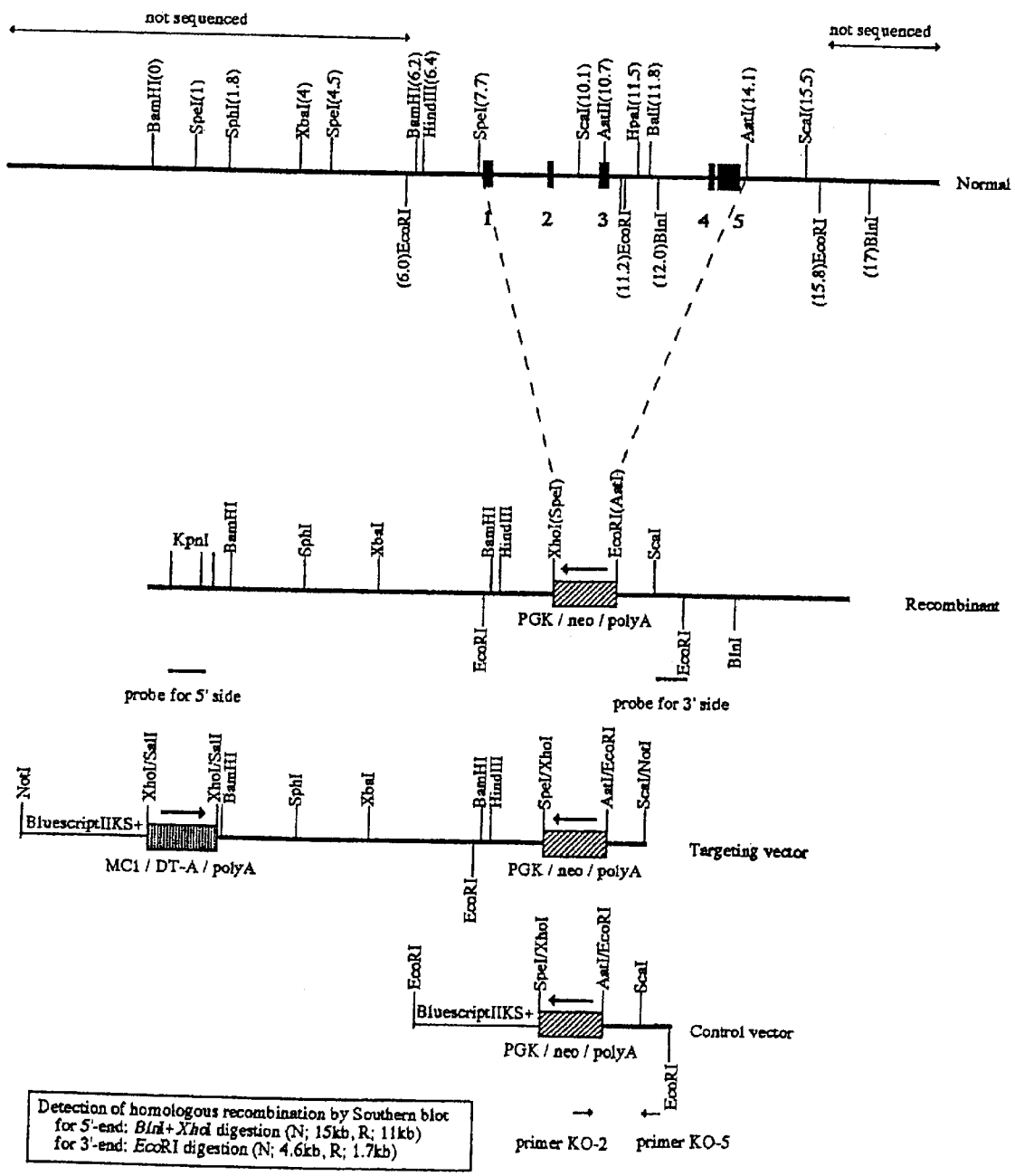
FIG. 1 shows the strategy of the targeting vector of the mouse with the LECT2 gene and the sites for reaction of probes.

When liver functions decrease in activities according to hepatic injury such as hepatitis, cirrhosis or hepatic cancer, cell proliferation of hepatocytes is started for recovery to get normal function of the hepatocytes with some cytokines. It is difficult to explain the regulation of cell proliferation of hepatocytes by only these cytokines. On the other hand, LECT2 expressed in hepatocytes in liver tissue may regulate liver functions, and LECT2 also relates with bone metabolism. It has not been clarified in detail, though some cytokines are related in these liver functions and bone metabolism.

Thus, it should be clarified in etiology of diseases related with dysfunctions of liver and bone according to the functions of LECT2 in vivo. Therefore, in order to analyze the role of LECT2 in vivo using a model animal lacking the LECT2 gene is strongly requested. The mouse prepared in this invention lacking the complete LECT2 gene by replacement of the gene with a gene lacking LECT2 or another gene, indicating the mouse has no LECT2 protein by lacking LECT2 gene in its partial or whole gene. The mouse in this invention is also concerned invention is also concerned with the mouse having a lack of the complete LECT2 gene in homozygotes or heterozygotes.

When liver functions decrease in activity according to hepatic injury such as hepatitis, cirrhosis or hepatic cancer, cell proliferation of hepatocytes is started for recovery to get normal function of the hepatocytes with some cytokines. It is difficult to explain the regulation of cell proliferation of hepatocytes by only these cytokines. On the other hand, LECT2 expressed in hepatocytes in liver tissue may regulate liver functions, and LECT2 also relates with bone metabolism. It has not been clarified in detail, though some cytokines are related in these liver functions and bone metabolism.

Thus, it should be clarified in the etiology of diseases related with dysfunctions of liver and bore according to the functions of LECT2 in vivo. Therefore, in order to analyze the role of LECT2 in vivo using a model animal lacking the LECT2 gene is strongly requested. The inventors prepare the mouse lacking the LECT2 gene. The mouse is prepared in this invention by replacing the gene with a gene lacking LECT2 or another gene, indicating the mouse has no LECT2 protein by lacking LECT2 gene in its partial or whole gene. The mouse in this invention is also concerned with the mouse having lack of the complete LECT2 gene in homozygotes or heterozygotes.

Preparation of targeting vector of the mouse LECT2 gene DNA

In order to prepare the mouse lacking LECT2 gene DNA LECT2 gene having, insertion, replacement of other gene(s), or its mutation is introduced into the wild (LECT2 (+/+)) mouse after screening of mouse LECT2 gene. For cloning, LECT2 gene chromosomal DNA is extracted from mouse tissue such as liver and DNA library by usual procedures is prepared, is estimated by screening products of polymerase chain reaction (PCR) prepared based, on nucleotide sequence of mouse LECT2 gene (Reference 10).

For lacking of LECT2 gene function, lack of whole LECT2 gene or insertion of other gene(s) into any site(s) of LECT2 gene is prepared. When other gene is inserted into LECT2 gene, insertion of marker gene(s) for other gene(s) is preferred to detect lacking LECT2 gene. For this purpose selection with resistance genes to genetisin (G418), neomycin (Neo), selection with gancyclobil resistance gene to herpes simple virus thymidine kinase (HSV-TK), or diphtheria toxin A fragment gene (DT-A) etc. is available. The insertion of these genes are proceeded by usual procedures in vitro. In this invention all exons of LECT2 gene are deleted and selection marker genes are inserted.

In detail positive clones are selected by hybridization with probes having partial sequence of LECT2 gene. These clones are inserted into a vector, and sub-clones having the specific exon in the chromosomal DNA are selected after digested with restriction enzymes. Targeting vector for positive and negative selection with marker gene(s) replaced by Neo, or DT-A genes) etc. to obtain lack of LECT2 gene is prepared.

LECT2 mutation in mouse embryonic stem cells (ES cells) by gene targeting

The targeting vector prepared above is inserted into ES cells homologous recombination in the ES cells, which are cell line having multi-potential and cultivated for maintain. The targeting vector is inserted with usual procedures such as electric pulse or aggregation. In this homologous recombination, DNA of LECT2 gene and site targeted area in targeting vector recombination, then the marker genes) are inserted into LECT2 gene in chromosomal LECT2 gene DNA, resulting in ES cells having lack of LECT2 gene and insertion of the marker gene(s). By selection of marker gene(s), ES cells lacking LECT2 gene are selected. For example, introduction of the gene by targeting vector and ES cells are mixed, and then selection culture for cloning ES cells lacking LECT2 gene with G418.

Preparation of chimera mice

The ES cells prepared above were introduced into the germinal folicle and then into the uterus of a mouse with pseudopregnancy. Thus, chimera mice from the mother are obtained, and then to make inbred with appropriate mouse strain to get infants. When progenitor cells of the chimera mouse are derived from the recombinant mouse lacking LECT2 gene, the mouse lacking the LECT2 gene is obtained.

Preparation of homozygote of LECT2 deficient mouse

Chimera mouse obtained with transplantation is inbred with planned mouse strain. Whether the character is derived from the chimera mouse or background strain mouse is determined with the appropriate characters of infants. Inbreeding of each heterozygote of LECT2 deficient mouse, and the infants are determined with Southern hybridization, resulting in obtaining the homozygote of the LECT2 deficient mouse. Procedures for keeping the mouse are not special and usual.

EXAMPLES

Explanation of practical example is shown as follow. Preparation of chimera mouse by aggregation procedures (References 11, 12) is described as follows, but this example is not a restriction of this invention.

Example 1

Cloning of Mouse Genomic Gene and Construction of the Targeting Vector

Mouse genome library was prepared from liver of 129/SvJ mouse. Mouse LECT2 gene and genomic DNA containing sequences in both terminal sides were cloned with probes of LECT2 cDNA in the wild/normal type. Subcloning of sequences in both terminal sides of LECT2 was preformed, and the targeting vector for positive and negative selections with Neo or DT-A was prepared (FIG. 1). FIG. 1 shows a scheme for mouse LECT2 gene and replaced gene. Wild-type LECT2(+/+), targeting vector and homologous recombination of LECT2 (Mutant allele), and also sites of PCR primers and 5' probes and 3' probes and restriction enzymes. In detail, target vector, which Neo and DT-A genes was inserted into LECT2 gene using as homologous site restriction enzyme BamHI-SpeI-digested fragment (7.7 kb, 5' site) and AatI-ScaI-digested fragment (1.a kb, 5' site) as homologous sites, was prepared. When homologous recombination occurs, whole length of LECT2 gene will be replaced into Neo cassette (1.6 kb).

Example 2

Preparation, Culture of ES Cells and Introduction of the Targeting Vector ES Cells E14.1 cell strain, which is sub-strain of E14 strain of ES cells derived from blastocyst of 129 strain mouse, was used for cells in order to introduce the targeting vector prepared as described in Example 1 (Reference 13). The ES cells were cultured with Dulbecco's modified minimal essential medium (DMEM) containing 15% fetal bovine serum (FBS), 0.1 mM 2-mercaptoetahnol, 0.35% glucose and 0.058 L-glutamine. Embryonic fibroblast cells (EF) for feeder cells were cultured with DMEM containing 7% FBS, 0.35% glucose and 0.058 L-glutamine. EF cells were transferred in a 3–4 days and were used for the feeder cells by treatment with mitomycin C (MMC). Confluent EF cells were treated with trypsin-EDTA (TE) for removal from the culture dish. After centrifugation, cell concentration was adjusted to $2$–$4 \times 10^4$ cells/cm$^2$, and then MMC was added. These cells were transferred to gelatin-coated flask, dish or micro-well plate. ES cells, were treated with TE for 5 minute at 37° C., dispersed with pipetting for preparation of a single-cell suspension, and plated on the feeder cell layer. Culture medium was changed in two days. The targeting vector was introduced into these ES cells with the procedures by Sudo and Iwakura (Reference 12). ES cells at a concentration of $1 \times 10^7$ cells and 20 μg of the targeting vector were mixed. DNA was inserted into ES cells with a electron polation of Shimadzu GTE-1 (250V, 500 μF, electrode distance, 0.2 cm). Cells treated with electric pulse for 5–7 msec were plated into a dish (10 cm diameter) coated with feeder cells. 24 hrs after the electric pulse, G418 at a concentration of 250 μg/ml was added into the culture. After 10 days, 96 colonies grew in the culture and were transferred into a 24-well plate, and cultured more and then collected. Half the number of cells were frozen in liquid nitrogen and others were used for extraction of genomic DNA for detection of recombination with southern hybridization. DNA extraction was performed by the usual procedures. Thus, colonies containing ES cells of homologous recombination were obtained.

Example 3

Selection of Cells Having Homologous Recombination

Cells having homologous recombination were determined with PCR and southern hybridization. As shown in FIG. 1, outside sequence of 3' of the targeting vector and inside sequence of Neo gene were used as PCR primers. 2 clones showing positive production with PCR were digested with restriction enzyme EcoRI, or BlnI/XhoI, and southern hybridization to confirm recombination in ES cells. Then, one clone only showed complete recombination. Thus, the obtained clone number was 1 in 320 showing G418 resistant clones.

Example 4

Preparation of Chimera Mouse and Selection of Mutant Mouse

After mating of C57BL/6 strain mice, blastocyst from the oviduct at 3.5th day was isolated and aggregated in a Tyrode buffer with ES cells having recombination. The aggregation was transferred into the uterus of mouse with psuedo-pregnancy. Infants of this tentative mother are chimera of C57BL/6-derived as a source of blastocyst, and 129-derived as a source of ES cells. Chimerisms was estimated with hair color. Infant mouse having higher contribution of 129 strain shows increase of rate of wild color or white, resulting in black-wild color and white stripe in hair color of the mouse. Seven chimera mice having right black color showing higher contribution of ES cells were selected, and made inbred with C56BL/6 mice. Tails of 33 of the infants having such a color were cut out for analysis of genotyping with the usual technique of the southern hybridization, resulting in obtaining 17 mice having heterozygote of LECT2 (LECT2(+/−)). Homozygote mouse (LECT2(−/−)) was obtained from a pair of heterozygotes (LECT2(−/−)).

Example 5

Expression of LECT2 Gene in LECT2 Deficient Mouse

Figure 2:
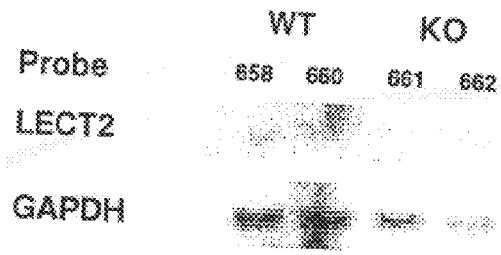
FIG. 2 shows Northern blot of LECT2.

Expression of mRNA of LECT2 in mouse with LECT2 gene deficiency in both alleles was measured. Whole RNA was isolated with the usual techniques from liver of mouse with LECT2(−/−), LECT2(+/−), or wild type (LECT2 (+/+)) as a control. The expression of LECT2 mRNA was determined with the Northern hybridization. LECT2 cDNA 280 bp was used for probe in the northern hybridization. LECT2 mRNA was not detected in LECT2(−/−) mice (FIG. 2). FIG. 2 shows Northern blot hybridization of LECT2 cDNA in order to compare the expression of LECT2 in hepatocytes in liver. The Northern blot by probe of GAPDH (glutaraldehyde dehydrogenase) shows control experiment for comparison of whole mRNA. WT: mRNA from liver of Wild-type, LECT2(+/+) mouse, K0: mRNA from liver of Knock-out, LECT2(−/−) mouse, The number shows mouse number. Moreover, Half amount of expression of LECT2 mRNA was determined in LECT2(+/−) compared with that in LECT2(−/−) mice.

Example 6

Based on the normal birth of animals, LECT2 gene does not seem to be essential for growth and development of mice. There is no difference in body weight between wild and LECT2(−/−) mice.

Example 7

Male and female with LECT2 gene deficiency were inbred to know the role of LECT2 on reproduction. As the next generation was born normally, LECT2 did not affect on the reproduction.

Example 8

Blood Examination was Performed to Know the Role of LECT2 in vivo

As the next generation was born normally, LECT2 did not affect on the reproduction. After taking whole blood from mouse with LECT2(−/−) and LECT2(+/+), blood examination was performed. Leukocyte counts decreased in LECT2 (−/−) mice than that in LECT2(+/+) mice. However, no remarkable differences in other data in the blood examination were observed.

TABLE 1

| | | | | | | | RBC × | | | | | | |
|---|---|---|---|---|---|---|---|---|---|---|---|---|---|
| Mouse No. | Genotype | Sex | ABIL mg/dl | AGOT IU/1/37° C. | AGPT IU/1/37° C. | AALB g/dl | 10000/ mm³ | WBC/ μl | HT % | MCV μ3 | HB g/dL | MCH pg | MCHC % |
| 428 | w.t. | Male | 0.3 | 74 | 41 | 2.2 | 594 | 17700 | 35.8 | 60 | 9.5 | 16 | 27 |
| 438 | w.t. | Male | 0.2 | 43 | 20 | 2.4 | 640 | 23200 | 37.7 | 59 | 10.9 | 17 | 29 |
| 429 | k.o. | Male | 0.2 | 48 | 26 | 3.2 | 889 | 12100 | 50.7 | 57 | 14.7 | 17 | 29 |
| 437 | k.o. | Male | 0.2 | 76 | 27 | 3 | 739 | 11000 | 45.1 | 61 | 13.8 | 19 | 31 |

Table header spanning: Blood cell counts and serological estimation of serum markers TABLE 1-continued Blood cell counts and serological estimation of serum markers

| Mouse No. | Genotype | Sex | ABIL mg/dl | AGOT IU/1/37° C. | AGPT IU/1/37° C. | AALB g/dl | RBC × 10000/ mm³ | WBC/ μl | HT % | MCV μ3 | HB g/dL | MCH pg | MCHC % |
|---|---|---|---|---|---|---|---|---|---|---|---|---|---|
| 431 | k.o. | Female | 0.3 | 62 | 34 | 3.3 | 705 | 20200 | 38.1 | 54 | 12.6 | 18 | 33 |
| 439 | k.o. | Female | 0.2 | 49 | 29 | 3.6 | 669 | 21500 | 37 | 55 | 11.4 | 17 | 31 |

Genotype is shown as w.t.: LECT2 wild type, k.o.: LECT2 gene deficiency (knock-out), AGOT: GOT activity, AGPT: GPT activity, ABIL: Total bilirubin, AALB: Total albumin RBC: number of red blood cells, WBC: number of white blood cells, HT: hematocrit, MCV: average red blood cell volume, HB: hemoglobin amount, MCH: average hemoglobin amount in red blood cells, MCHC: average hemoglobin concentration in red blood cells.

After taking blood from mouse, blood cell counts and serological markers were measured according to the clinical examinations.

Example 9

Organ Observations of Mutant Mouse

Histological staining of various organs were observed for investigation of the role of LECT2 gene deficiency. Hepatocytes in liver were stained weak in hematoxylin and eosin (HE) staining and plural nucleus in a cell (Table 2). However, no typical differences in other organs and tissues were observed.

TABLE 2

Histological straining various organs.

| Organs | Mouse No. | | | | | |
|---|---|---|---|---|---|---|
| Findings | 428 | 429 | 431 | 437 | 438 | 439 |
| Genotype | w.t. | k.o. | k.o. | k.o. | w.t. | k.o. |
| Sex | Male | Male | Female | Male | Male | Female |
| Cerebrum | 0 | 0 | 0 | 0 | 0 | 0 |
| Cerebellum | 0 | 0 | 0 | 0 | 0 | 0 |
| Heart | 0 | 0 | 0 | 0 | 0 | 0 |
| Liver | | | | | | |
| Single cell necrosis | 1 | 0 | 0 | 0 | 0 | 0 |
| Extramedullary hematopoiesis | 2* | 1** | 3*** | 0 | 2* | 2** |
| Kidney | | | | | | |
| Mononuclear cell infiltration, interstitial | 0 | 0 | 0 | 0 | 1 | 0 |
| Mononuclear cell infiltration, pelvic | 0 | 0 | 1B | 0 | 1U | 0 |
| Muscle | 0 | 0 | / | 0 | 0 | 0 |
| Lung | | | | | | |
| Mononuclear cell infiltration, perivascular | 0 | 0 | 1 | 0 | 0 | 0 |
| Spleen | | | | | | |
| Extramedullary hematopoieses | 3 | 1 | 3 | 3 | 3 | 3 |
| Lymphocyte depletion, periarterial lymphoid sheath | 0 | 0 | 3 | 0 | 0 | 0 |
| Bone + Bone marrow Granulopoiesis, increased | 0 | 0 | / | 0 | 1 | 0 |
| Testis | | | | | | |

TABLE 2-continued

Histological straining various organs.

| Organs | Mouse No. | | | | | |
|---|---|---|---|---|---|---|
| Findings | 428 | 429 | 431 | 437 | 438 | 439 |
| Degeneration/necrosis, spermatid/spermatocyte | 2 | 1 | / | 0 | 0 | / |

0: no remarkable change, 1: slight, 2: mild, 3: moderate, 4: severe
B. bilateral
U: unilateral
*granulocytic and erytrhoblastic,
**erythroblastic,
***granulocyteic Example 10

Liver Functions of Mutant Mouse

Figure 3A:
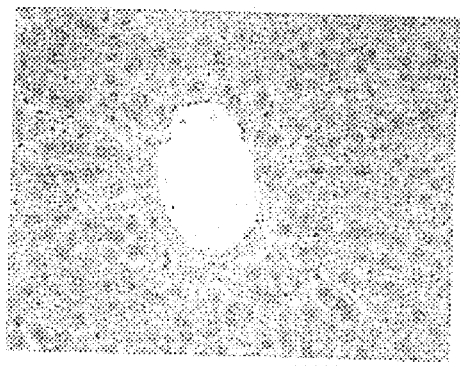
FIGS. 3a and 3b show a histochemistry of the liver.
Figure 3B:
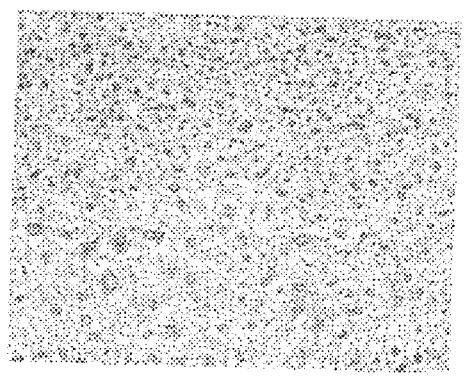

Liver tissue was observed histologically. Liver producing LECT2 shows a different size in hepatocytes and an increase of cells having a shrinked nucleus and two nuclei than that of a wild mouse. These results show that regulation of cell proliferation and cell death in LECT2(−/−) mouse is not normal (FIG. 3). FIG. 3 shows micrograph of liver tissue stained with hematoxyline and eosin (HE). FIG. 3a shows LECT2(+/+) mouse, and FIG. 3b LECT2(−/−) mouse. The liver tissue was stained weakly in LECT2(−/−) and mouse had many hepatocytes having 2 nucleus.

Example 11

Hepatocytes having a shrinked nucleus is whether apoptotic cell or not was observed using the procedures of TUNEL (terminal deoxynucleotidyl transferase-mediated dUTP-biotin nick end labeling) (Reference 14). According to these procedures, DNA fragmentation as a biochemical marker of apoptosis can be detected. Cell number showing apoptosis in LECT2(−/−) mice increased by 2–5 fold than that of LECT2(+/+) mice (FIG. 4). Based on these results, metabolic abnormality in the liver of mouse lacking LECT2 gene seems to have occurred.

Figure 4A:
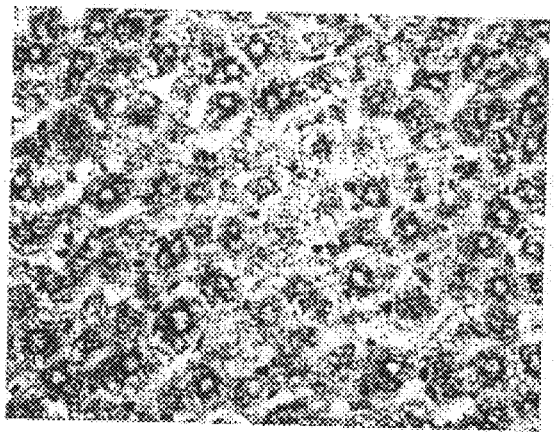
FIGS. 4a and 4b show apoptosis of cells in liver.
Figure 4B:
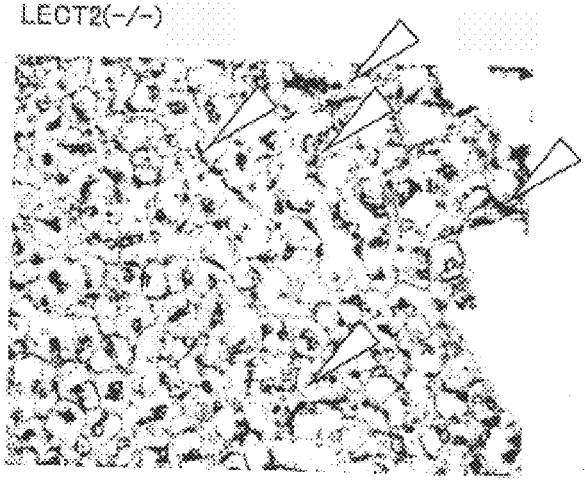

FIG. 4a shows micrograph of TUNEL stain of liver in LECT2 (+/+) mouse and FIG. 4b LECT2(−/−) mouse. Apoptotic cells were stained brown colored (open arrow). In LECT2(+/+) mouse it wa-a-not seen, but in LECT2(−/−) mouse it was observed.

Example 12

Induction of apoptosis of hepatocytes in LECT2(−/−) mouse suggests that LECT2 is an important cytokine for cell proliferation of liver tissue.

Example 13

The difference in cell proliferation and apoptosis between LECT2(+/+) mouse and LECT2(−/−) mouse is interesting in a role of the cell proliferation and apoptosis in liver.

Effect of the Invention

As described above, this invention gives the mouse lacking the complete LECT2 gene by replacing of Neo gene etc. This mouse is useful for investigation of pathophysiology, etiology, evaluation of medication of diseases, which are related with LECT2, hepatitis, hepatic cancer, cirrhosis, regeneration of liver tissue, autoimmune diseases, rheumatoid arthritis, osteoporosis, abnormality of bone metabolism, nephritis, vascular diseases, atherosclerosis, ischemic dysfunction and the development of new protocols for treatments.

Disease features of patients with hepatitis, hepatic cancer, regeneration of liver tissue, rheumatoid arthritis, abnormality of bone metabolism, brain diseases, nephritis, vascular diseases, artherosclerosis, and ischemic dysfunction are not good. Therefore, an effective medication has been required. Since evaluation for new drugs should be examined in vivo, LECT2(−/−) mice will be expected for the purpose.

LECT2 and other cytokines can become stimulants to induce some diseases; hepatitis, hepatic cancer, regeneration of liver tissue, rheumatoid arthritis, abnormality of bone metabolism, brain diseases, nephritis, vascular diseases, atherosclerosis, and ischemic dysfunction. However, LECT2 has never been reported to induce these diseases in vivo. LECT2(−/−) mouse, which has been developed in this invention, is useful for analyses of inflammatory diseases and etiology of the diseases described above in vivo, and for analyses of induction mechanisms of inflammatory diseases and the diseases described above. In addition, it is also useful for the development of new drugs for these diseases.

REFERENCES

1. Tsubouchi, H., Kawakami, S., Hirono, S., Miyazaki, H., Kimoto, M., Arima, T., Sekiyama, K., Yoshiba, M., Arakaki, N. and Daikuhara, Y. Predication of outcome in fulminant hepatic failure by serum human hepatocyte growth factor (letter) Lancet 340, 307, 1992.
2. Yamada, Y., Kirillova, I., Peschon, J. J. and Fausto, N. Initiation of liver growth by tumor necrosis factor: Deficient liver regeneration in mice lacking type I tumor necrosis factor receptor. Proc. Natl. Acad. Sci. USA, 94, 1441–1446, 1997.
3. Cressman, D. E., Greenbaum, L. E., Deangelis, R. A., Ciliberto, G., Furth, E. E., Poli, V. and Taub, R. Liver failure and defective hepatocyte regeneration in interleukin-6deficient mice. Science 274, 1379–1383, 1996.
4. Yamagoe, S., Akasaka, T., Uchida, T., Hachiya, T., Okabe, T., Yamakawa, Y., Arai, T., Mizuno, S. and Suzuki, K. Expression of a neutrophil chemotactic protein LECT2 in human hepatocytes revealed by immunochemical studies using polyclonal and monoclonal antibodies to a recombinant LECT2. Biochem. Biophys. Res. Commun. 237, 116–120, 1997.
5. Yamagoe, S., Yamakawa, Y., Matsuo, Y., Minowada, J., Mizuno, S. and Suzuki, K. LECT2: Purification of novel human neutrophil chemotactic protein. Immunol. Lett. 52, 9–13, 1996.
6. H. Nagai, T. Hamada, T. Uchida, S. Yamagoe, K. Suzuki. Systemic expression of a newly recognized protein, LECT2, in human body Pathology International*48, 882–886, 1998.
7. T. Uchida, H. Nagai, K. Gotoh, H. Kanagawa, H. Kouyama, T. Kawanishi, S. Mima, S. Yamagoe and K. Suzuki. Expression pattern of newly
8. Y. Mori, Y. Hiraki, C. Shukunami, S. Kakudo, M. Skiokawa, M. Kagoshima, H. Mano, Y. Hakeda, T. Kurokawa, F. Suzuki, M. Kumegawa. FEBS Lett 406, 310–314, 1997.
9. Smithies O., Gregg, R. G., Boggs, S. S., Koralewski, M. A. and Kucherlapati, R. S. Insertion of DNA sequences into the human chromosomal b-globinlocusby homologous recombination. Nature 317: 230–234, 1985.
10. S. Yamagoe, T. Watanabe, S. Mizuno, K. Suzuki. The Mouse LECT2 Gene: Cloning of a cDNA, Structural Characterization and Chromosomal Localization. Gene 216, 171–178, 1998.
11. Nagy, A., Rossant, J., Nagy, R., Abramow-Newcrely, W. and Roder, J. Derivation of completely cell culture-derived mice from early-passage embyonic stem cells. Proc. Natl. Acad. Sci. USA. 90, 8424–8428, 1993.
12. Sudo, K., Iwakura, Y., Preparation of mutant mouse using aggregation method in Jikken Igaku Suppl. "New handbook of new gene technology the 3rd edition", pp. 250–256, 1999.
13. Kuhn, R., Rajewsky, K. and Muller, W. Generation and analysis of Interleukin-4deficientmice.science 254, 707–710, 1991.
14. Gavrieli, Y., Sherman, Y., Ben, S. S. Identification of programmed cell death in situ via specific labeling of nuclear DNA fragmentation. J. Cell Biol. 119, 493–501, 1992.

What is claimed is:

1. A genetically modified mouse whose genome comprises a homozygous disruption of the LECT2 gene such that production of functional LECT2 protein is inhibited and wherein said mouse exhibits decreased numbers of leukocytes as compared to a wild type mouse.

2. The genetically modified mouse of claim 1 wherein said disruption is an insertion of a selectable marker gene.

3. A genetically modified mouse whose genome comprises a homozygous disruption of the LECT2 gene such that production of functional LECT2 protein is inhibited and wherein said mouse exhibits an increased level of apoptosis in hepatocytes.

4. The genetically modified mouse of claim 3 wherein said disruption is an insertion of a selectable marker gene.

* * * * *